US005814450A

United States Patent [19]
Stanley et al.

[11] Patent Number: 5,814,450
[45] Date of Patent: Sep. 29, 1998

[54] USE OF MULTIVALENT INORGANIC CATIONS IN THE ELECTROCHEMICAL TREATMENT OF NUCLEIC ACID

[75] Inventors: Christopher J. Stanley, St. Ives; Patricia L. Archer, Cambridge, both of England

[73] Assignee: Scientific Generics Ltd., Cambridge, England

[21] Appl. No.: 759,646

[22] Filed: Dec. 5, 1996

Related U.S. Application Data

[62] Division of Ser. No. 256,784, Nov. 18, 1994, Pat. No. 5,607,832.

[30] Foreign Application Priority Data

Jan. 23, 1992 [GB] United Kingdom .................... 9201481

[51] Int. Cl.$^6$ ............................... C12Q 1/68; C12P 19/34
[52] U.S. Cl. ........................... 435/6; 435/91.1; 435/91.2; 436/94
[58] Field of Search .............................. 435/6, 91.1, 91.2, 435/91.52, 810; 436/94

[56] References Cited

U.S. PATENT DOCUMENTS

| | | | |
|---|---|---|---|
| 4,683,202 | 7/1987 | Mullis | 435/91.2 |
| 4,787,963 | 11/1988 | MacConnell | 204/180.1 |
| 4,945,045 | 7/1990 | Forrest et al. | 435/25 |
| 5,527,670 | 6/1996 | Stanley | 435/6 |

FOREIGN PATENT DOCUMENTS

| | | |
|---|---|---|
| 201184 | 12/1986 | European Pat. Off. . |
| 320308 | 6/1989 | European Pat. Off. . |
| WO9204470 | 3/1992 | WIPO . |

OTHER PUBLICATIONS

Palecek: "Electrochemical Behaviour of Biological Macromolecules", Bioelectrochemistry and Bioenergetics, 15, (1986) 275–295, A section of J. Electroanal. Chem. and constituting vol. 211, (1986).

Brabec, et al: "Interaction of Nucleic Acids with Electrically Charged Surfaces II, Conformational Changes in Double–Helical Polynucleotides", Biophysical Chemistry 4 (1976) 79–92.

Brabec: "Interaction of Nucleic Acids with Electrically Charged Surfaces. VI. A Compartive Study on the Elecrochemical Behaviour of Native and Denatured DNAs at Graphite Electrodes", Biophysical Chemistry 9 (1979) 289–297.

Brabec: "Raman Scattering From Nucleic Acids Absorbed at a Silver Electrode", Biophysical Chemistry, 23 (1985) 63–70.

Harris et al: "Synthesis of meso–Substituted Porphyrins", J.C.S. Chem. Comm. 1977, pp. 771–772.

Boublikova et al: "Absorptive Stripping Voltammetry of DNA", Studia Biophysica vol. 114 (1980) No. 1–3, pp. 83–90.

Palecek, et al: "Cyclic Voltammetry of Nucleic Acids and Determination of Submicrogram Quantities of Deoxyribonucleic Acids by Adsorptive Stripping Voltammetry", Analytica Chimica Acts, 187 (1986) 99–107.

Palecek, et al: "Absence of Unwinding of Double–Helical DNA in the Surface of Mercury Electrode Charged to DNA Reduction Potentials at Neutral pH", Part V in the series Interaction of Nucleic Acids with Electrically Charged Surfaces; Part IV: J. Electroanal. Chem Interfacial Electrochem, 88, 373 (1978) pp. 448–455.

Palecek, et al: "Electrochemical analysis of the self–complementry B–DNA decamer d(CCAGGCCTGG)", Bioelectrochemistry and Bioenergetics, 23 (1990) 285–299.

Brabec, et al: "Interactions of Nucleic Acids with Electrically Charged Surfaces—Part IV. Local Changes in the Structure of DNA Adsorbed on Mercury Electrode in the Vicinity of Zero Charge", J. Electroanal. Chem., 88 (1978) 373–385.

Jelen, et al: "Nucleotide Sequence–Dependent Opening of Double–Stranded DNA at an Electrically Charged Surface", Gen. Physiol. Biophys. (1985) 4, 219–237.

Stanley, et al:"Amperometric Enzyme–Amplified Immunoassays", Joural of Immunological Methods, 112 (1988) 153–161.

"Bioelectrochemistry and Bioenergetics", J Electroanal Chem., vol. 156, Nos. 2 and 3, pp. 245–255.

Nurnberg, H.W. "the Electrochemical Behavior of DNA at Electrically Charged Interfaces", Biophysics of Structure and Mechanism, vol. 1 No. 1, 1974, pp. 17–26.

Viktor Brabec, Nucleic Acid Analysis by Voltammetry at Carbon Electrodes, Bioelectrochemistry and Bioenergetic 8(1981) 437–449.

Emil Palecek, "Adsorptive Transfer Stripping Voltrammetry: Determination of Nanogram Quantities of DNA Immobilized at the Electrode Surface", Analytical Biochem. 170, 421–431 (1988).

Emil Palacek, "New trends in electrochemical analysis of nucleic acids", Bioelectrochem. and Bioenergetics, 20 (1988) 179–194.

E. Palacek, "Modern Polarographic (Voltammetric) Techniques in Biochemistry and Molecular Biology", Topics in Bioelectrochemistry and Bioenergetics vol. 5 pp. 118–155.

(List continued on next page.)

Primary Examiner—Kenneth R. Horlick
Attorney, Agent, or Firm—Townsend and Townsend and Crew LLP

[57] ABSTRACT

A process is described for denaturing native double-stranded nucleic acid material into its individual strands in an electrochemical cell. The process is an electrical treatment of the nucleic acid with a voltage applied to the nucleic acid material by an electrode. The process employs a promoter which is an inorganic multivalent cation such as a magnesium ion to speed denaturation. The process may be used in the detection of nucleic acid by hybridizing with a labelled probe or in the amplification of DNA by a polymerase chain reaction or ligase chain reaction.

20 Claims, 1 Drawing Sheet

OTHER PUBLICATIONS

Hermann Berg, "Polarographic Possilibities in Protein and Nucleic Acid Research", Academy of Science of GDR, pp. 44–44–103.

Mary Lou Fultz et al "Mediator Compounds for the Electrochemical Study of Biological Redox Systems: A Compilation", Organic Analytical Research Division, (1982).

Frantisek Jelen et al "Chemically Reversible Electroreduction of Guanine in a Polynucleotide Chain", Biophysical Chemistry 24 (1986) 285–290.

T. Pawlowski et al, "Some Aspects of the Copper(II)–DNA Interation", ACTA Biochimica Polonica, vol. 36 (1989) No. 1, 75–85.

Hans Wolfgang Nurnberg, "Applications of Advanced Voltammetric Methods in Bioelectrochemistry", Instit. of Applied Physical Chemistry, pp. 183–225.

F.A. Walker et al, "Effect of heme orientation on the reduction potential of cytochrome b5", J Am Chem. Soc. USA, 1988 110/18 (6234–6240).

Acta Biochimica Polonica, vol. 36, No. 1, 1989, Warsaw, PL pp. 75–85, Pawlowski T. et al, see the whole document.

Emil Palecek, "Adsorptive transfer stripping voltammetry: effect of electrode potential on the structure of DNA adsorbed at the mercury surface", Bioelectrochemistry and Bioenergetics, 28 (1992) 71–83, J. Electroanal Chem., vol. 343 (1992).

USE OF MULTIVALENT INORGANIC CATIONS IN THE ELECTROCHEMICAL TREATMENT OF NUCLEIC ACID

This application is a divisional application of U.S. patent application Ser. No. 08/256,784, filed on Nov. 18, 1994 which issued on Mar. 4, 1997 as the U.S. Pat. No. 5,607,832 patent, which is incorporated herein by reference in its entirety for all purposes.

FIELD OF THE INVENTION

This invention relates to processes for the treatment of nucleic acid material in order to effect a complete or partial change from double stranded form to single stranded form and to processes of amplifying or detecting nucleic acids involving such denaturation processes.

BACKGROUND OF THE INVENTION

Double stranded DNA (deoxyribonucleic acid) and DNA/RNA (ribonucleic acid) and RNA/RNA complexes in the familiar double helical configuration are stable molecules that, in vitro, require aggressive conditions to separate the complementary strands of the nucleic acid. Known methods that are commonly employed for strand separation require the use of high temperatures of at least 60° celsius and often 100° celsius for extended periods of ten minutes or more or use an alkaline pH of 11 or higher. Other methods include the use of helicase enzymes such as Rep protein of *E. coli* that can catalyse the unwinding of the DNA in an unknown way, or binding proteins such as 32-protein of *E. coli* phage T4 that act to stabilise the single stranded form of DNA. The denatured single stranded DNA produced by the known processes of heat or alkali is used commonly for hybridisation studies or is subjected to amplification cycles.

U.S. Pat. No. 4,683,202 (Kary B Mullis et al, assigned to Cetus Corporation) discloses a process for amplifying and detecting a target nucleic acid sequence contained in a nucleic acid or mixture thereof by separating the complementary strands of the nucleic acid, hybridising with specific oligonucleotide primers, extending the primers with a polymerase to form complementary primer extension products and then using those extension products for the further synthesis of the desired nucleic acid sequence by allowing hybridisation with the specific oligonucleotides primers to take place again. The process can be carried out repetitively to generate large quantities of the required nucleic acid sequence from even a single molecule of the starting material. Separation of the complementary strands of the nucleic acid is achieved preferably by thermal denaturation in successive cycles, since only the thermal process offers simple reversibility of the denaturation process to reform the double stranded nucleic acid, in order to continue the amplification cycle. However the need for thermal cycling of the reaction mixture limits the speed at which the multiplication process can be carried out owing to the slowness of typical heating and cooling systems. It also requires the use of special heat resistant polymerase enzymes from thermophilic organisms for the primer extension step if the continuous addition of heat labile enzyme is to be avoided. It limits the design of new diagnostic formats that use the amplification process because heat is difficult to apply in selective regions of a diagnostic device and it also can be destructive to the structure of the DNA itself because the phosphodiester bonds may be broken at high temperatures leading to a collection of broken single strands. It is generally believed that the thermophilic polymerases in use today have a lower fidelity ie. make more errors in copying DNA than do enzymes from mesophiles. It is also the case that thermophilic enzymes such as TAQ polymerase have a lower turnover number than heat labile enzymes such as the Klenow polymerase from *E. coli*. In addition, the need to heat to high temperatures, usually 90° celsius or higher to denature the nucleic acid leads to complications when small volumes are used as the evaporation of the liquid is difficult to control. These limitations have so far placed some restrictions on the use of the Mullis et al process in applications requiring very low reagent volumes to provide reagent economy, in applications where the greatest accuracy of copy is required such as in the Human Genome sequencing project and in the routine diagnostics industry where reagent economy, the design of the assay format and the speed of the DNA denaturation/renaturation process are important.

Denaturation/renaturation cycles are also required in order to perform the so-called ligase chain reaction described in EP-A-0320308 in which amplification is obtained by ligation of primers hybridised to template sequences rather than by extending them.

It is known that DNA has electrochemical properties. For example, N. L. Palacek (in "Electrochemical Behaviour of Biological Macromolecules", Bioelectrochemistry and Bioenergetics, 15, (1986), 275–295) discloses the electrochemical reduction of adenine and cytosine in thermally denatured single stranded DNA at about –(minus) 1.5V on the surface of a mercury electrode. This reduction process also requires a prior protonation and therefore takes place at a pH below 7.0. The primary reduction sites of adenine and cytosine form part of the hydrogen bonds in the Watson-Crick base pairs. Palacek was unable to demonstrate reduction of adenine and cytosine in intact, native double stranded DNA at the mercury electrode. Palacek has further demonstrated that to a very limited extent the DNA double helix is opened on the surface of the mercury electrode at a narrow range of potentials centred at –(minus) 1.2 V in a slow process involving an appreciable part of the DNA molecule. This change in the helical structure of the DNA is thought to be due to prolonged interaction with the electrode charged to certain potentials and is not thought to be a process involving electron transfer to the DNA. No accumulation of single stranded DNA in the working solution was obtained and no practical utility for the phenomenon was suggested. Palacek also reports that the guanine residues in DNA can be reduced at –(minus) 1.8 V to dihydroguanine which can be oxidised back to guanine at around –(minus) 0.3 V. The reducible guanine double bond is not part of the hydrogen bonds in the Watson-Crick base pairs and this electrochemical process involving guanine does not affect the structure of the DNA double helix.

In an earlier paper F. Jelen and E. Palacek (in "Nucleotide Sequence-Dependent Opening of Double-Stranded DNA at an Electrically Charged Surface", Gen. Physiol. Biophys., (1985), 4, pp 219–237), describe in more detail the opening of the DNA double helix on prolonged contact of the DNA molecules with the surface of a mercury electrode. The mechanism of opening of the helix is postulated to be anchoring of the polynucleotide chain via the hydrophobic bases to the electrode surface after which the negatively charged phosphate residues of the DNA are strongly repelled from the electrode surface at an applied potential close to –(minus) 1.2 V, the strand separation being brought about as a result of the electric field provided by the cathode. There is no disclosure of separating the strands of the DNA double helix while the DNA is in solution (rather than adsorbed onto the electrode) and there is no disclosure of useful amounts of single strand DNA in solution. Furthermore, there is no disclosure that the nucleotide base sequence of the DNA on the electrode is accessible from solution. The bases themselves are tightly bound to the mercury surface. A mercury electrode is a complex system and the electrode can only be operated in the research laboratory with trained technical staff.

H. W. Nurnberg ("Applications of Advanced Voltammetric Methods in Electrochemistry" in "Bioelectrochemistry", Plenum Inc (New York), 1983, pp. 183–225) discloses partial helix opening of adsorbed regions of native DNA to a mercury electrode surface to form a so-called ladder structure. However, the DNA is effectively inseparably bound to or adsorbed onto the electrode surface. In this condition, we believe the denatured DNA to be of no use for any subsequent process of amplification or analysis. To be of any use, the denatured DNA must be accessible to subsequent processes and this is conveniently achieved if the single stranded DNA is available in free solution or is associated with the electrode in some way but remains accessible to further processes. Nurnberg has not demonstrated the ability of the mercury electrode to provide useful quantities of single stranded DNA.

V. Brabec and K. Niki ("Raman scattering from nucleic acids adsorbed at a silver electrode" in Biophysical Chemistry (1985), 23, pp 63–70) have provided a useful summary of the differing views from several workers on DNA denaturation at the surface of both mercury and graphite electrodes charged to negative potentials. There has emerged a consensus amongst the research workers in this field that the denaturation process only takes place in DNA that is strongly adsorbed to the electrode surface and only over prolonged periods of treatment with the appropriate negative voltage, a positive voltage having no effect on the double helix.

Brabec and Palacek (J. Electroanal. Chem., 88 (1978) 373–385) disclose that sonicated DNA damaged by gamma radiation is transiently partially denatured on the surface of a mercury pool electrode, the process being detectable by reacting the single stranded products with formaldehyde so as to accumulate methylated DNA products in solution. Intact DNA did not show any observable denaturation.

Our Application No. PCT/GB91/01563 discloses a process for denaturing double-stranded nucleic acid which comprises operating on solution containing nucleic acid with an electrode under conditions such as to convert a substantial portion of said nucleic acid to a wholly or partially single stranded form.

This process was based on a finding that it is possible to produce the denaturation of undamaged (i.e. non-irradiated) DNA at ambient temperature by applying a suitable voltage to a solution in which the DNA is present under suitable conditions.

The mechanism for the process has not yet been fully elucidated. We believe that the process is one in which the electric field at the electrode surface which produces the denaturation of the double helix.

In polymerase chain reaction processes, it has been shown that the denatured DNA produced by the denaturing process is immediately in a suitable state for primer hybridisation and extension. On a larger scale, it has been found that samples of denatured DNA produced either by a negative voltage electrode or thermal denaturation can be caused or encouraged to reanneal by incubation at a higher temperature or by the use of a positive voltage.

Although the process of Application No. PCT/GB91/01563 can take place in a solution containing only the electrode and the nucleic acid dissolved in water containing a suitable buffer, the process can be facilitated by the presence in the solution containing the nucleic acid of a promoter compound. Methyl viologen or a salt thereof was disclosed as the preferred promoter compound.

It is believed that the positively charged viologen molecules interact between the negatively charged DNA and the negatively charged cathode to reduce electrostatic repulsion therebetween and hence to promote the approach of the DNA to the electrode surface where the electrical field is at its strongest. Accordingly, we expressed a preference in Application No. PCT/GB91/01563 to employ as promoters compounds having spaced positively charged centres, e.g. bipolar positively charged compounds. Preferably, the spacing between the positively charged centres was to be similar to that in viologens.

SUMMARY OF THE INVENTION

We have now discovered that multivalent inorganic cations, preferably $Mg^{2+}$, can also act as promoters in such a system with approximately the same efficacy as methyl viologen.

It is thought that large cations such as $Mg^{2+}$ are able to act as a bridge between a negative electrode and negatively charged regions of the double-stranded nucleic acid.

Accordingly, the present invention provides a process for denaturing double-stranded nucleic acid which comprises operating on solution containing said nucleic acid with an electrode under condition such as to convert a substantial proportion of said nucleic acid to a wholly or partially single stranded form wherein the solution contains an effective concentration of a multivalent inorganic cation acting as a promoter which assists said denaturation.

DESCRIPTION OF THE PREFERRED EMBODIMENTS

The cations used as the promoter may include inorganic cations complexed with inorganic or organic ligands, e.g. $Pt(NH_3)_6^{4+}$ and $Cr(NH_3)_6^{2+}$ but the preferred cation is $Mg^{2+}$. Mixtures of promoter cations may be employed.

The concentration of said promoter cation is preferably from 1 mM to 250 mM, more preferably from 70 mm, e.g. about 100 mM.

Preferably, according to the invention, the single stranded nucleic acid produced is free from the electrode, e.g. in solution. However, the nucleic acid may be immobilised on the electrode in double or single stranded form prior to the application of the electric potential, e.g. attached by the end or a small portion intermediate the ends of the nucleic acid chain, so as to leave substantial segments of the nucleic acid molecules freely pendant from the electrode surface before and after denaturation.

In addition to said electrode and a counter-electrode, a reference electrode may be contacted with said solution and a voltage may be applied between said electrode and said counter-electrode so as to achieve a desired controlled voltage between said electrode and said reference electrode. The electrodes may be connected by a potentiostat circuit as is known in the electrochemical art.

Preferably, a potential of from −0.5 to −1.5 V is applied to said working electrode with respect to said reference electrode, more preferably from −0.8 to −1.1 V, e.g. about 1.0 V.

Working electrode voltages are given throughout as if measured or as actually measured relative to a calomel reference electrode (BDH No. 309.1030.02).

The ionic strength of said solution is preferably no more than 250 mM, more preferably no more than 100 mM. As it has been found that the rate of denaturation increases as the ionic strength is decreased, the said ionic strength is still more preferably no more than 50 mM, e.g. no more than 25 mM or even no more than 5 mM. Generally, the lower the ionic strength, the more rapid is the denaturation. However, in calculating ionic strength for these purposes it may be appropriate to ignore the contribution to ionic strength of any component which acts as a promoter as described above.

The process may be carried out in an electrochemical cell of the type described by C. J. Stanley, M. Cardosi and A. P. F. Turner "Amperometric Enzyme Amplified Immunoassays" J. Immunol. Meth (1988) 112, 153–161 in which there is a working electrode, a counter electrode and optionally a reference electrode. The working electrode at or by which the denaturing nucleic acid is effected may be of any convenient material e.g. a noble metal such as gold or platinum, or a glassy carbon electrode.

The electrode may be a so called "modified electrode" in which the denaturing is promoted by a compound coated onto, or adsorbed onto, or incorporated into the structure of the electrode which is otherwise of an inert but conducting material. In an alternative electrochemical cell configuration the working, counter and reference electrodes may be formed on a single surface e.g. a flat surface by any printing method such as thick film screen printing, ink jet printing, or by using a photo-resist followed by etching. It is also possible that the counter and reference electrodes can be combined on the flat surface leading to a two electrode configuration. Alternatively the electrodes may be formed on the inside surface of a well which is adapted to hold liquid. such a well could be the well known 96 well or Microtitre plate, it may also be a test tube or other vessel. Electrode arrays in Microtitre plates or other moulded or thermoformed plastic materials may be provided for multiple nucleic acid denaturation experiments.

The strand separation may be carried out in an aqueous medium or in a mixture of water with an organic solvent such as dimethylformamide. The use of polar solvents other than water or non-polar solvents is also acceptable but is not preferred. The process may be carried out at ambient temperatures or if desired temperatures up to adjacent the pre-melting temperature of the nucleic acid. The process may be carried out at pH's of from 3 to 10 conveniently about 7. Generally, more rapid denaturation is obtained at lower pH. For some purposes therefore a pH somewhat below neutral, e.g about pH 5.5 may be preferred. The nucleic acid may be dissolved in an aqueous solution containing a buffer whose nature and ionic strength are such as not to interfere with the strand separation process.

The denaturing process according to the invention may be incorporated as a step in a number of more complex processes, e.g. procedures involving the analysis and or the amplification of nucleic acid. Some examples of such applications are described below.

The invention includes a process for detecting the presence or absence of a predetermined nucleic acid sequence in a sample which comprises: denaturing a sample double-stranded nucleic acid by means of a voltage applied to the sample in a solution by means of an electrode; hybridising the denatured nucleic acid with an oligonucleotide probe for the sequence; and determining whether the said hybridisation has occurred, wherein during denaturing the solution contains an effective concentration of a multivalent inorganic cation acting as a promoter which assists said denaturation.

Thus, the invented process has application in DNA and RNA hybridisation where a specific gene sequence is to be identified e.g. specific to a particular organism or specific to a particular hereditary disease of which sickle cell anaemia is an example. To detect a specific sequence it is first necessary to prepare a sample of DNA, preferably of purified DNA, means for which are known, which is in native double stranded form. It is then necessary to convert the double stranded DNA to single stranded form before a hybridisation step with a labelled nucleotide probe which has a complementary sequence to the DNA sample can take place. The denaturation process of the invention can be used for this purpose in a preferred manner by carrying out the following steps:

denaturing a sample of DNA by applying a voltage by means of an electrode to the sample DNA with a said promoter in solution;

hybridising the denatured DNA with a directly labelled or indirectly labelled nucleotide probe complementary to the sequence of interest; and determining whether the hybridisation has occurred, which determination may be by detecting the presence of the probe, the probe being directly radio-labelled, fluorescent labelled, chemiluminescent labelled or enzyme-labelled or being an indirectly labelled probe which carries biotin for example to which a labelled avidin or avidin type molecule can be bound later.

In a typical DNA probe assay it is customary to immobilise the sample DNA to a membrane surface which may be composed of neutral or charged nylon or nitrocellulose. The immobilisation is achieved by charge interactions or by baking the membrane containing DNA in an oven. The sample DNA can be heated to high temperature to ensure conversion to single stranded form before binding to the membrane or it can be treated with alkali once on the membrane to ensure conversion to the single stranded form. The disadvantages of the present methods are:

heating to high temperatures to create single stranded DNA can cause damage to the sample DNA itself.

the use of alkali requires an additional step of neutralisation before hybridisation with the labelled probe can take place.

One improved method for carrying out DNA probe hybridisation assays is the so called "sandwich" technique where a specific oligonucleotide is immobilised on a surface. The surface having the specific oligonucleotide thereon is then hybridised with a solution containing the target DNA in a single-stranded form, after which a second labelled oligonucleotide is then added which also hybridises to the target DNA. The surface is then washed to remove unbound labelled oligonucleotide, after which any label which has become bound to target DNA on the surface can be detected later.

This procedure can be simplified by using the denaturing process of the invention to denature the double-stranded DNA into the required single-stranded DNA. The working electrode, counter electrode and optionally a reference electrode and/or the promoter can be incorporated into a test tube or a well in which the DNA probe assay is to be carried out. The DNA sample, promoter if not already present and oligonucleotide probes can then be added and the voltage applied to denature the DNA. The resulting single-stranded DNA is hybridised with the specific oligonucleotide immobilised on the surface after which the remaining stages of a sandwich assay are carried out. All the above steps can take place without a need for high temperatures or addition of alkali reagents as in the conventional process.

The electrochemical denaturation of DNA can be used in the amplification of nucleic acids, e.g. in a polymerase chain reaction or ligase chain reaction amplification procedure. Thus the present invention provides a process for replicating a nucleic acid which comprises: separating the strands of a sample double stranded nucleic acid in solution under the influence of an inorganic multivalent cation promoter and an electrical voltage applied to the solution from an electrode; hybridising the separated strands of the nucleic acid with at least one oligonucleotide primer that hybridises with at least one of the strands of the denatured nucleic acid; synthesising an extension product of the or each primer which is sufficiently complementary to the respective strand of the nucleic acid to hybridise therewith; and separating the or each extension product from the nucleic acid strand with which it is hybridised to obtain the extension product.

In such a polymerase mediated replication procedure, e.g. a polymerase chain reaction procedure, it may not be necessary in all cases to carry out denaturation to the point of producing wholly single-stranded molecules of nucleic acid. It may be sufficient to produce a sufficient local and/or temporary weakening or separation of the double helix in the primer hybridisation site to allow the primer to bind to its target. Once the primer is in position on a first of the target strands, rehybridisation of the target strands in the primer region will be prevented and the other target strands may be progressively displaced by extension of the primer or by further temporary weakening or separation processes.

Preferably, the said amplification process further comprises repeating the procedure defined above cyclicly, e.g. for more than 10 cycles, e.g. up to 20 or 30 cycles. In the amplification process the hybridisation step is preferably carried out using two primers which are complementary to different strands of the nucleic acid.

The denaturation to obtain the extension products as well as the original denaturing of the target nucleic acid is preferably carried out by applying to the solution of the nucleic acid a voltage from an electrode, the solution containing a promoter as described therein.

The process may be a standard or classical PCR process for amplifying at least one specific nucleic acid sequence contained in a nucleic acid or a mixture of nucleic acids wherein each nucleic acid consists of two separate complementary strands, of equal or unequal length, which process comprises:

(a) treating the strands with two oligonucleotide primers, for each different specific sequence being applied, under conditions such that for each different sequence being amplified an extension product of each primer is synthesised which is complementary to each nucleic acid strand, wherein said primers are selected so as to be substantially complementary to different strands of each specific sequence such that the extension product synthesised from one primer, when it is separated from its complement, can serve as a template for synthesis of the extension produce of the other primer:

(b) separating the primer extension products from the templates on which they were synthesised to produce single-stranded molecules in the presence of a said promoter by applying a voltage from an electrode to the reaction mixture: and (c) treating the single-stranded molecules generated from step (b) with the primers of step (a) under conditions such that a primer extension product is synthesised using each of the single strands produced in step (b) as a template.

Alternatively, the process may be any variant of the classical or standard PCR process, e.g. the so-called "inverted" or "inverse" PCR process or the "anchored" PCR process.

The invention therefore includes an amplification process as described above in which a primer is hybridised to a circular nucleic acid and is extended to form a duplex which is denatured by the denaturing process of the invention, the amplification process optionally being repeated through one or more additional cycles.

More generally, the invention includes a process for amplifying a target sequence of nucleic acid comprising hybridisation, amplification and denaturation of nucleic acid (e.g. cycles of hybridising and denaturing) wherein said denaturation is produced by operating on a solution containing said nucleic acid with an electrode in the presence of an inorganic multivalent cation promoter.

The process of the invention is applicable to the ligase chain reaction. Accordingly, the invention includes a process for amplifying a target nucleic acid comprising the steps of:

(a) providing nucleic acid of a sample as single-stranded nucleic acid;

(b) providing in the sample at least four nucleic acid probes, wherein: i) the first and second of said probes are primary probes, and the third and fourth of said probes are secondary nucleic acid probes; ii) the first probe is a single strand capable of hybridising to a first segment of a primary strand of the target nucleic acid; iii) the second probe is a single strand capable of hybridising to a second segment of said primary strand of the target nucleic acid; iv) the 5' end of the first segment of said primary strand of the target is positioned relative to the 3' end of the second segment of said primary strand of the target to enable joining of the 3' end of the first probe to the 5' end of the second probe, when said probes are hybridised to said primary strand of said target nucleic acid; v) the third probe is capable of hybridising to the first probe; and iv) the fourth probe is capable of hybridising to the second probe; and (c) repeatedly or continuously: i) hybridising said probes with nucleic acid in said sample; ii) ligating hybridised probes to form reorganised fused probe sequences; and iii) denaturing DNA in said sample by applying a voltage from an electrode to the reaction mixture in the presence of a said promoter.

In all of the amplification procedures described above the denaturation of the DNA to allow subsequent hybridisation with the primers can be carried out by the application of an appropriate potential to the electrode. The process may be carried out stepwise involving successive cycles of denaturation or renaturation as in the existing thermal methods of PCR and LCR, but it is also possible for it to be carried out continuously since the process of chain extension or ligation by the enzyme and subsequent strand separation by the electrochemical process can continue in the same reaction as nucleic acid molecules in single-stranded form will be free to hybridise with primers once they leave the denaturing influence of the electrode. Thus, provided that the primer will hybridise with the DNA an extension or ligation product will be synthesised. The electrochemical DNA amplification technique can be used analytically to detect and analyse a very small sample of DNA eg a single copy gene in an animal cell or a single cell of a bacterium.

The invention includes a kit for use in a process of detecting the presence or absence of a predetermined nucleic acid sequence in a sample which kit comprises, an electrode, a counter electrode and optionally a reference electrode, an oligonucleotide probe for said sequence and a source of an inorganic multivalent cation for use as a promoter in obtaining nucleic acid strand separation at said electrode. The probe may be labelled in any of the ways discussed above.

The invention also includes a kit for use in a process of nucleic acid amplification comprising an electrode, a counter electrode and optionally a reference electrode, and a source of an inorganic multivalent cation for use as a promoter in obtaining nucleic acid strand separation at said electrode and at least one primer for use in a PCR procedure, or at least one primer for use in an LCR procedure, and/or a polymerase or a ligase, and/or nucleotides suitable for use in a PCR process.

Preferably, such kits includes a cell containing the electrodes. Preferably the kits include a suitable buffer for use in the detection or amplification procedure.

BRIEF DESCRIPTION OF THE DRAWING

The invention will now be described with reference to the following drawings and examples.

In FIG. 1 there is shown a cell structure 10 comprising a working compartment 12 in which there is a body of DNA-containing solution, a working electrode 14, a counter electrode 16, a FiVac seal 19, a Kwik fit adaptor 21 and a magnetic stirrer 18. A reference electrode 20 in a separate side arm is connected via a "luggin" capillary 23 to the solution in the working compartment 12. The working electrode, counter electrode and reference electrode are connected together in a potentiostat arrangement so that a constant voltage is maintained between the working electrode 14 and the reference electrode 20. Such potentiostat arrangements are well known (see for example "Instrumental Methods in Electrochemistry" by the Southampton Electrochemistry Group, 1985, John Wiley and Sons, p 19).

Figure 1:
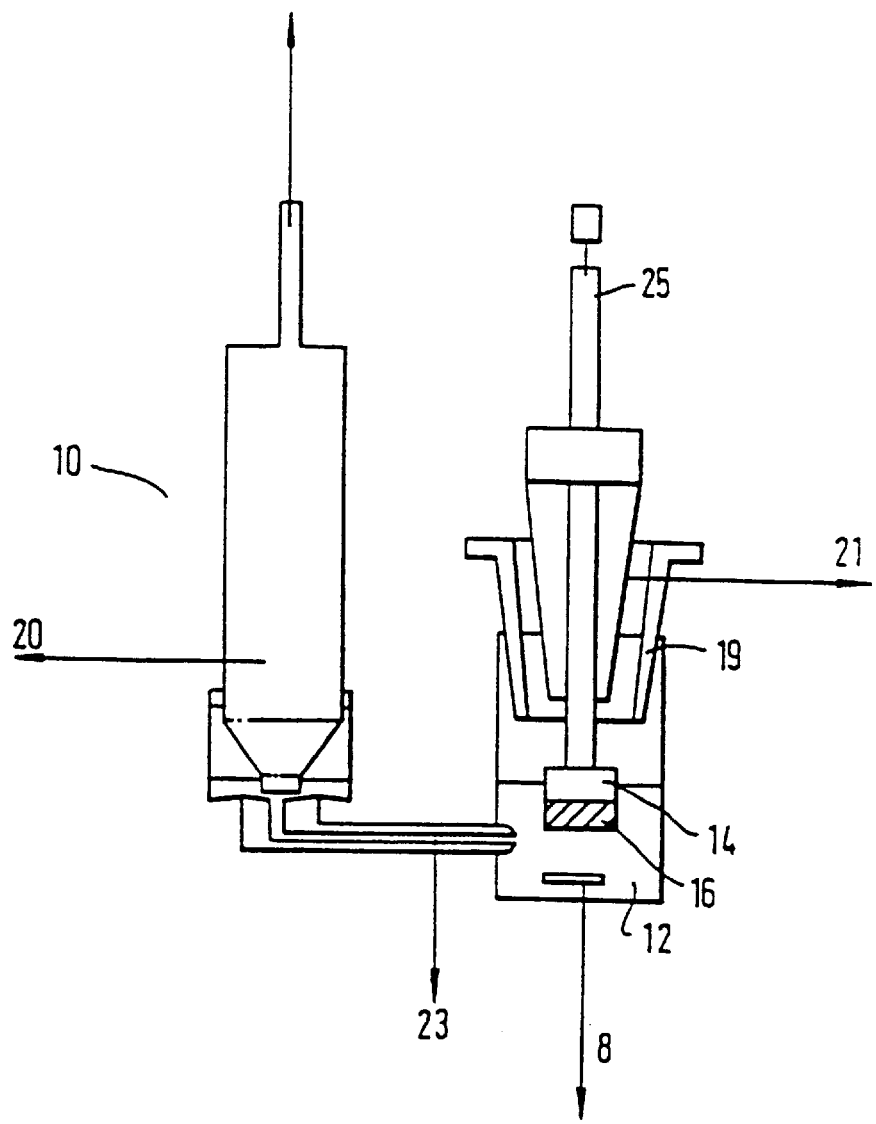
FIG. 1 is a diagram of an electrochemical cell used for denaturation of DNA.

The electrode 14 is a circular glassy carbon rod of diameter 0.5 cm, narrowing to 0.25 cm at a height of 10 mM, and having an overall length of 9 cm inside a teflon sleeve of outside diameter 0.8 cm (supplied by Oxford Electrodes, 18 Alexander Place, Abingdon, Oxon), and the reference electrode 16 is a 2 mm pin calomel (supplied by BDH No 309/1030/02). The counter electrode is supported by a wire which is soldered to a brass sleeve 25 above the adaptor and passes down and exits the teflon sleeve 20 mm from the base of the working electrode. The wire attaches to a cylindrical platinum mesh counter-electrode supplied by Oxford Electrodes which annularly surrounds the working electrode.

This cell is used in the following examples.

EXAMPLE 1

To the working chamber of the cell shown in FIG. 1 was added 900 μl of distilled water and 40 μg/ml of Calf Thymus DNA together with the promoter shown in Table 1 below. The contents of the cell were subjected to −1.0V for up to 4 hours.

Samples were taken at 0, 30 mins, 1 hr, and 2 hrs. from commencement and analysed on 1% agarose gel to observe the degree of denaturation. Results were as shown in Table 1.

| Run | Promoter | Promoter Concentration | Time for complete denaturation |
| --- | --- | --- | --- |
| 1 | Mg Cl$_2$ | 10 mM | >4 hrs |
| 2 | " | 30 mM | >4 hrs |
| 3 | " | 100 mM | 1–2 hours |

-continued

| Run | Promoter | Promoter Concentration | Time for complete denaturation |
| --- | --- | --- | --- |
| Control | Methyl Viologen | 30 mg/ml (120 mM approx) | 1–2 hours |

Thus it can be seen that in this system a minimum effective amount of $Mg^{2+}$ as a promoter lies between 30 and 100 mM and that $Mg^{2+}$ is approximately as effective as a promoter as methyl viologen.

We claim:

1. A process for amplifying a target sequence of nucleic acid comprising hybridisation, replication and denaturation of nucleic acid, wherein said hybridisation and said denaturation are produced by applying a voltage to a solution containing said nucleic acid with an electrode and wherein the solution contains an effective concentration of a multivalent inorganic cation acting as a promoter which assists said denaturation.

2. The process as claimed in claim 1, which is a polymerase chain reaction amplification process or a ligase chain reaction amplification process.

3. A process for replicating a nucleic acid which comprises: separating the strands of a sample double-stranded nucleic acid in solution to effect a denaturation under the influence of an electrical voltage applied to the solution from an electrode; hybridising the separated strands of the nucleic acid with at least one oligonucleotide primer that hybridises with at least one of the strands of the denatured nucleic acid by applying an electrical voltage to the solution from an electrode; synthesising an extension product of the or each primer which is sufficiently complementary to the respective strand of the nucleic acid to hybridise therewith; and separating the or each extension product from the nucleic acid strand with which it is hybridised to obtain the extension product wherein the solution contains an effective concentration of a multivalent inorganic cation acting as a promoter which assists said denaturation.

4. The process as claimed in claim 3, which further involves repeating the procedure defined in claim 3 cyclicly.

5. The process as claimed in claim 3, wherein the hybridisation step is carried out using two primers which are complementary to different strands of the nucleic acid.

6. The process as claimed in claim 3, wherein the separating to obtain the extension product is carried out by applying to a solution of the extension product a voltage from an electrode.

7. The process as claimed in claim 3, for amplifying at least one specific nucleic acid sequence contained in a nucleic acid or a mixture of nucleic acids wherein each nucleic acid consists of two separate complementary strands, of equal or unequal length, which process comprises:

(a) treating the strands with two oligonucleotide primers, for each different specific sequence being amplified, under conditions such that for each different sequence being amplified an extension product of each primer is synthesised which is complementary to each nucleic acid strand, wherein said primers are selected so as to be substantially complementary to different strands of each specific sequence such that the extension product synthesised from one primer, when it is separated from its complement, can serve as a template for synthesis of the extension product of the other primer;

(b) separating the primer extension products from the templates on which they were synthesised to produce single-stranded molecules by applying a voltage from an electrode to the reaction mixture wherein the reaction mixture contains an effective concentration of a multivalent inorganic cation acting as a promoter for said separation; and (c) treating the single-stranded molecules generated from step (b) with the primers of step (a) under conditions such that a primer extension product is synthesised using each of the single strands produced in step (b) as a template.

8. The process as claimed in claim 2 for amplifying a target nucleic acid comprising the steps of:

(a) providing nucleic acid of a sample as single-stranded nucleic acid;

(b) providing in the sample at least four nucleic acid probes, wherein: i) the first and second of said probes are primary probes, and the third and fourth of said probes arc secondary nucleic acid probes; ii) the first probe is a single strand capable of hybridising to a first segment of a primary strand of the target nucleic acid; iii) the second probe is a single strand capable of hybridising to a second segment of said primary strand of the target nucleic acid; iv) the 5' end of the first segment of said primary strand of the target is positioned relative to the 3' end of the second segment of said primary strand of the target to enable joining of the 3' end of the first probe to the 5' end of the second probe, when said probes are hybridised to said primary strand of said target nucleic acid; v) the third probe is capable of hybridising to the first probe; and iv) the fourth probe is capable of hybridising, to the second probe; and (c) repeatedly or continuously: i) hybridising said probes with nucleic acid in said sample; ii) ligating hybridised probes to form reorganised fused probe sequences; and iii) denaturing DNA in said sample by applying a voltage from an electrode to the reaction mixture, wherein the reaction mixture contains an effective concentration of a multivalent inorganic cation acting as a promoter for said separation.

9. A process for detecting the presence or absence of a predetermined nucleic acid sequence in a sample which comprises: denaturing a sample double-stranded nucleic acid by applying a voltage to the sample in a solution from an electrode, wherein the solution contains an effective concentration of a multivalent inorganic cation acting as a promoter which assists said denaturation; hybridising the denatured nucleic acid with an oligonucleotide probe for the sequence by applying a voltage to the sample in the solution from an electrode; and determining whether the said hybridisation has occurred.

10. A kit for use in a process of nucleic acid amplification said kit comprising:
an electrode,
a counter electrode
a source of inorganic multivalent cation, for use as a promoter in obtaining nucleic acid strand separation at said electrode, and
more than one primer for use in a polymerase chain reaction (PCR) procedure or a ligase chain reaction (LCR) procedure.

11. The kit of claim 10, further comprising a polymerase or a ligase.

12. The kit of claim 10, further comprising nucleotides suitable for use in a PCR procedure.

13. The kit of claim 10, further comprising a reference electrode.

14. A kit for use in a process of nucleic acid amplification, said kit comprising:

(a) an electrode, (b) a counter electrode, (c) a source of inorganic multivalent cation for use as a promoter in obtaining nucleic acid strand separation at said electrode, (d) at least one primer for use in a polymerase chain reaction (PCR) procedure, and (e) a polymerase.

15. The kit of claim 14, further comprising nucleotides suitable for use in a PCR procedure.

16. The kit of claim 14, further comprising a reference electrode.

17. A kit for use in a process of nucleic acid amplification, said kit comprising:

(a) an electrode, (b) a counter electrode, (c) a source of inorganic multivalent cation for use as a promoter in obtaining nucleic acid strand separation at said electrode, (d) at least one primer for use in a ligase chain reaction (LCR) procedure, and (e) a ligase.

18. The kit of claim 17, further comprising a reference electrode.

19. The kit of claim 17, further comprising nucleotides suitable for use in an LCR procedure.

20. A process for denaturing and annealing two complementary nucleic acid strands comprising the steps of:

(a) applying a negative voltage to a solution containing a double-stranded nucleic acid with an electrode such that at least a proportion of said double-stranded nucleic acid is denatured to wholly or partially single-stranded nucleic acid, wherein the solution contains an effective concentration of a multivalent inorganic cation acting as a promotor which assists said denaturing process; and (b) applying a positive voltage to said solution with an electrode to cause said wholly or partially single-stranded nucleic acid to anneal with a complementary nucleic acid strand.

* * * * *